United States Patent
Oksymets et al.

(10) Patent No.: US 10,821,206 B2
(45) Date of Patent: Nov. 3, 2020

(54) HUMAN CELL-BASED MEDICINAL PRODUCTS AND METHODS FOR OSTEOREPARATION

(71) Applicant: ILAYA USA CORPORATION, San Jose, CA (US)

(72) Inventors: Volodymyr Mykhaylovych Oksymets, Donets'k (UA); Dmytro Oleksandrovych Zubov, Donets'k (UA); Roman Hennadiyovych Vasyliev, Makiivka (UA)

(73) Assignee: ILAYA USA CORPORATION, San Jose, CA (US)

( * ) Notice: Subject to any disclaimer, the term of this patent is extended or adjusted under 35 U.S.C. 154(b) by 0 days.

(21) Appl. No.: 15/538,616

(22) PCT Filed: Nov. 4, 2016

(86) PCT No.: PCT/UA2016/000128
§ 371 (c)(1),
(2) Date: Jun. 21, 2017

(87) PCT Pub. No.: WO2017/078654
PCT Pub. Date: May 11, 2017

(65) Prior Publication Data
US 2017/0348461 A1 Dec. 7, 2017

(30) Foreign Application Priority Data
Nov. 4, 2015 (UA) .................................. 2015 10734

(51) Int. Cl.
| | | |
|---|---|---|
| *A61L 27/38* | (2006.01) | |
| *A61L 27/52* | (2006.01) | |
| *A61L 27/22* | (2006.01) | |
| *A61L 27/24* | (2006.01) | |
| *A61L 27/36* | (2006.01) | |

(52) U.S. Cl.
CPC ......... *A61L 27/3821* (2013.01); *A61L 27/225* (2013.01); *A61L 27/24* (2013.01); *A61L 27/365* (2013.01); *A61L 27/3608* (2013.01); *A61L 27/3654* (2013.01); *A61L 27/3834* (2013.01); *A61L 27/3847* (2013.01); *A61L 27/3852* (2013.01); *A61L 27/3886* (2013.01); *A61L 27/52* (2013.01); *A61L 2430/02* (2013.01); *A61L 2430/06* (2013.01)

(58) Field of Classification Search
CPC ............. A61L 27/3821; A61L 27/3654; A61L 27/3886; A61L 27/3834; A61L 27/3852; A61L 27/3847; A61L 27/52; A61L 27/225; A61L 27/24; A61L 27/3608; A61L 27/365; A61L 2430/06; A61L 2430/02; A61P 19/00
See application file for complete search history.

(56) References Cited

U.S. PATENT DOCUMENTS

| | | |
|---|---|---|
| 2008/0262632 A1 | 10/2008 | Panasyuk |
| 2012/0003185 A1 | 1/2012 | Meretzki |
| 2012/0087958 A1 | 4/2012 | Dufrane et al. |
| 2015/0037436 A1* | 2/2015 | Huang ................... A61K 35/35 424/574 |

FOREIGN PATENT DOCUMENTS

| | | |
|---|---|---|
| CN | 102350009 A | 2/2012 |
| KR | 1020000050294 | 8/2000 |
| RU | 2147800 C1 | 4/2000 |
| RU | 2278679 C1 | 6/2006 |
| RU | 2279281 C1 | 7/2006 |
| RU | 2273489 C1 | 12/2008 |
| RU | 2342162 C1 | 12/2008 |
| RU | 2343934 C1 | 1/2009 |
| RU | 24955667 C1 | 10/2013 |
| SU | 1357012 A1 | 12/1987 |
| UA | 108813 C2 | 6/2015 |
| WO | 2015159308 A2 | 10/2015 |

OTHER PUBLICATIONS

Correia et al. In Vitro Model of Vascularized Bone: Synergizing Vascular Development and Osteogenesis. PLoS ONE 6(12): e28352S (Year: 2011).*

(Continued)

*Primary Examiner* — Taeyoon Kim
(74) *Attorney, Agent, or Firm* — Cantor Colburn LLP

(57) ABSTRACT

Method of the osteoreparative processes' correction and/or bone defect restoration by means of human cell-based products (cell and/or tissue transplants) and the method of its manufacturing. The invention a creates and establishes conditions for osteoreparative processes restoration in destroyed bone tissue by osteoreparation cell sources restoration as the result of use cell technologies and bone tissue engineering methods, e.g. scaffold-guided regeneration, particularly by means of cell transplantation by injection and/or transplantation of original three-dimensional osteoreparative prevascularized graft (3D-OPG). Manufacturing of medical products and preparations of the product based on human cells (cell and/or tissue transplants) is dedicated for impaired osteoreparative processes correction and/or bone defect restoration.

17 Claims, 3 Drawing Sheets

(56) References Cited

OTHER PUBLICATIONS

Duttenhoefer et al. 3D Scaffolds Co-Seeded With Human Endothelial Progenitor and Mesenchymal Stem Cells: Evidence of Prevascularisation Within 7 Days. European Cells and Materials. vol. 26, p. 49-65. (Year: 2013).*

Grellier et al. Role of Vascular Endothelial Growth Factor in the Communication Between Human Osteoprogenitors and Endothelial Cells. Journal of Cellular Biochemistry 106:390-398 (Year: 2009).*

Hoffman et al. Emulating Native Periosteum Cell Population and Subsequent Paracrine Factor Production to Promote Tissue Engineered Periosteum-Mediated Allograft Healing. Biomaterials. Jun. 2015; 52: 426-440. (Year: 2015).*

Kneser et al. Engineering of Vascularized Transplantable Bone Tissues: Induction of Axial Vascularization in an Osteoconductive Matrix Using an Arteriovenous Loop. Tissue Engineering. vol. 12, No. 7, 2006. p. 1721-1731 (Year: 2006).*

International Search Report for International Application No. PCT/UA2016/000128; International Filing Date Nov. 4, 2016; dated Mar. 14, 2017; 3 pages.

Written Opinion for International Application No. PCT/UA2016/000128; International Filing Date Nov. 4, 2016; dated Mar. 14, 2017; 7 pages.

Asahar, Takayuki., et al., "Isolation of Putative Progenitor Endothelial Cells for Angiogenesis", Science Feb. 14, 1997, vol. 275, Issue 5302, pp. 964-966.

Reale, Antonia, et al., "Functional and Biological Role of Endothelial Precursor Cells in Tumour Progression: A New Potential Therapeutic Target in Haematological Malignancies", Stem Cells International, 2016, Article ID 7954580, 11 pages.

Vasyliev, R.G., et al., "Tissue-Engineered Bone for Treatment of Combat Related Limb Injuries", Exp. Oncol. 2017 39(3); pp. 191-196.

Yoder, Mervin C., "Human Endothelial Progenitor Cells", Cold Spring Harb Perspect Med. Jul. 2012;2(7):a006692, 14 pages.

Oksymets V et al., Use of cultured autologous BM-MSCs for altered post-traumatic reparative osteogenesis treatment: nonrandomized clinical trial, World Conference on Regenerative Medicine, Leipzig, Oct. 21-23, 2013, Regenerative Medicine 2013 8(6S):47-48.

Zhao et al., "Treatment of early stage osteonecrosis of the femoral head with autologous implantation of bone marrow-derived and cultured mesenchymal stem cells", Elsevier, Bone 50 (2012) 325-330.

Oksymets V et al., Clinical use of human-cultured, autologous, bone marrow-derived MSCs for treatment of the femoral head avascular necrosisl, World Conference on Regenerative Medicine, Leipzig, Oct. 21-23, 2013, Regenerative Medicine 2013 8(6S):226-227.

Vasyliev R et al., Stem cell-based therapy and tissue engineering for traumatology and orthopedics : our experience in civil and war time, ISCT Regional Meeting, Seville (Spain), Sep. 24-26, 2015 : Program Abstracts, p. 66-67.

Zubov D et al., Tissue-engineered bone equivalent for combat casualty cure, World Conference on Regenerative Medicine, Leipzig, Oct. 21-23, 2015 : Meeting Abstracts, Regenerative Medicine, 2015, vol. 10, No. 07s.—p. 159.

* cited by examiner

HUMAN CELL-BASED MEDICINAL PRODUCTS AND METHODS FOR OSTEOREPARATION

This application is a national stage of International Application No.: PCT/UA2016/000128, which was filed on Nov. 4, 2016, and which claims priority to UA 201510734 which was filed on Nov. 4, 2015, and which are both herein incorporated by reference.

BACKGROUND OF THE INVENTION

Field of the Invention

The invention relates to regenerative medicine and biotechnology, as well as traumatology and orthopedics, veterinary medicine and can be used for cell therapy or bone tissue engineering for subsequent transplantation with the aim to restore defects of bone tissue of both humans and animals as well as to restore impaired osteoreparative processes caused by the trauma, the femoral head or other bones' blood circulation impairments.

Description of the Background Art Cell/tissue transplants or products/preparations based on cord blood, other human tissues and cells in accordance with the laws of Ukraine [the law of Ukraine No. 1007-XIV dd. Jul. 7, 1999. On the transplantation of organs and other anatomical human materials, the Order of the Ministry of Health of Ukraine No 630 dd. Oct. 10, 2007 On Approval of the Procedure for Conducting Clinical Trials of Medicinal Products and Expert Evaluation of Materials Pertinent to Clinical Trials and amendments to the Procedure for Conducting Clinical Trials of Medicinal Products and Expert Evaluation of Materials Pertinent to Clinical Trials approved by the order of the Ministry of health of Ukraine dd. Feb. 13, 2006 No. 66 registered in the Ministry of Justice of Ukraine on Mar. 10, 2006 under No. 252/12126"; License conditions of the operating of the business activity of the cord blood banks, other human tissues and cells banks];

Human cell-based medicinal products those in terms of the European Medicines Agency, EMEA correspond to the definition of Human Cell-Based Medicinal Products (CBMP)» [EMEA/CHMP Guideline on Human Cell-Based Medicinal Products (EMEA/CHMP/410869/2006)];

Human cells, tissues, and cellular and tissue-based products those in terms of the USA Food and Drug Administration (FDA) correspond to the definition of Human cells, tissues, and cellular and tissue-based products (HCT/Ps) [21CFR1271. Code of Federal Regulations. Title 21 Food and drugs. Chapt. I—Food and Drug Administration: Department of health and human services. Subchapt. L—Regulations under certain other acts administered by the Food and Drug Administration. Part 1271—Human cells, tissues, and cellular and tissue-based products: Subpart D—Current Good Tissue Practice.—[valid from Jan. 19, 2001, revised as of Apr. 1, 2011].—Title 21, Vol. 8.—66 FR 5466, Jan. 19, 2001].

It is known the false joints treatment method. The transplant is administered into the surgery area of false joint. The transplant is fabricated as demineralized allogeneic transplant of tubular bone seeded with autologous mesenchymal stem cells (multipotent mesenchymal stromal/stem cells, MSCs) with cell density of $7\text{-}10\times10^6/cm^3$. In case of osteoplasty the biotransplant is located in the bone groove after false joint resection or saving treatment of bone fragments to bleeding, and additionally the biotransplant was located paraossally and was of the size sufficient to cover the bone groove formed, then it was fixed with circular sutures. It allows creating conditions for the additional bone formation areas [Patent of Russian federation RU No 2309756«A method of treating false joints by transplantation of autologous mesenchymal stem cells biotransplantat for its application»]. The disadvantage of the method is that a biotransplant located in the area contains non osteogenic induced MSCs. Instead of inducing influence of the periosteum and endosteum cells, it may form the cells of non-specific connective tissue. Another disadvantage of this method is absence of time for quick bio transplant vascularization that may cause a death of the significant part of cells placed on the demineralized allogeneic bone.

It is known the femoral head avascular osteonecrosis treatment method. The area of osteonecrosis I or II after the decompression groove formation by means of the bone trepan and its closure by bone wax with cultured $2\times10^6$ bone marrow-derived MSCs in form of suspension. Foe example, see "Treatment of early stage osteonecrosis of the femoral head with autologous implantation of bone marrow-derived and cultured mesenchymal stem cells," Dewei Zhao, Daping Cui, Benjie Wang, Fengde Tian, Lin Guo, Lei Yang, Baoyi Liu, Xiaobing Yu//Bone.—2012.—No. 50.—P. 325-330. The disadvantage of the method is that the cultured cells are administered into the osteonecrosis area in form of suspension that weaken bone structure formation in the area of cells infusion. Another disadvantage of this method is that coverage of the decompression groove by bone wax prevents reduction of the intrabone pressure and restoration of the blood supply in the affected area of femoral head.

SUMMARY OF THE INVENTION

The developed method involves the creation of conditions for restoration of the osteoreparative processes in the affected bone tissue by means of restoring the post-surgical cell sources that is achieved with use of cell technologies and bone tissue engineering methods (cell-seeded scaffold-guided regeneration), in particular by means of injection transplantation of the cells or transplantation of the original 3D osteoprogenitor prevascularized graft (3D-OPG).

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
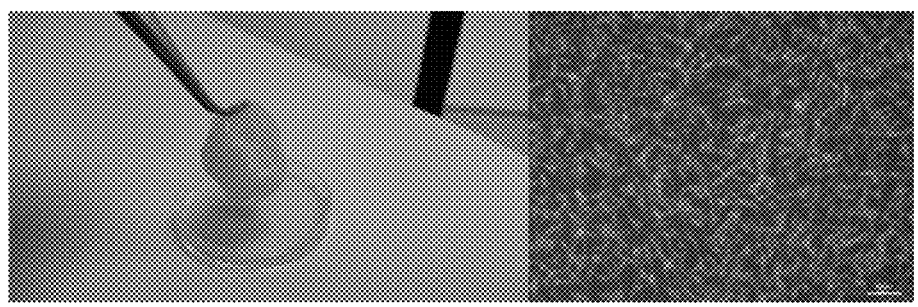
FIG. 1: shows 3D-OPG component view—fibrin hydrogel (on the left) and microphotograph of fibrin hydrogel seeded with cultured cells (on the right); FDA/PI combined stain (quality control on cell seeding efficiency and cell viability).

The Method can be Divided into the Following Stages

1. Anatomic material taking at the surgery/procedure room: bone marrow aspiration, fragment of subcutaneous fat/lipoaspirate, bone fragment, peripheral blood venipuncture.
2. Cell isolation, culturing and expansion in the biotechnology lab: bone marrow-derived multipotent mesenchymal stromal/stem cells (MSCs), adipose-derived MSCs, or adipose-derived stem cells, ADSCs, periosteum cells, and endothelial progenitor cells. Manufacturing of the 3D osteoprogenitor prevascularized graft (3D-OPG) at the biotechnology lab.
3. Storage of the cultured cells under ultra-low temperatures.
4. Transplantation of the 3D-OPG at the surgery room in case of fracture non-unions (false joints), bone defects and femoral head avascular osteonecrosis.

STAGE 1 should be performed as follows:
I. Anatomic material taking at the surgery/procedure room: bone marrow aspiration, fragment of subcutaneous fat/lipoaspirate, bone fragment, peripheral blood venipuncture
1. In a surgery room during the cerebrospinal and/or regional anesthesia or its combination, the surgical area should be treated with an antiseptic solution in the area of front upper iliac wing edge (right or left side) and/or collarbone. With the needle for bone marrow puncture the puncture was made through the skin, subcutaneous fat, cortical bone for 1-1.5 cm; the syringe pre-filled with anticoagulant is used for aspiration of the red bone marrow in the volume required 0.5 ml-100 ml.
2. In a surgery room during the cerebrospinal and/or anesthesia or its combination, the surgical area should be treated with an antiseptic solution in the sampling field, for instance, in the middle third of the outer surface of the right or left leg, the skin is cut to the sufficient size by the scalpel. Fibula bone is exposed by means of surgery tools. The fibula bone is sampled in the size required, for instance, 1.0×0.2×0.2 cm fragment, by means of a chisel.
3. In a surgery room during the cerebrospinal and/or anesthesia or its combination, the surgical area should be treated with an antiseptic solution in the sampling field, for instance, 1-2 punctures are made in the area of the anterior abdominal wall using 18 G needle. Through obtained ports-pricks, vacuum syringe extraction of subcutaneous fat is performed as lipoaspirate in volume of 1 ml to 200 ml or more with the help of cannula, for instance, 2.4 mm in diameter.
4. In a surgery room during the cerebrospinal and/or anesthesia or its combination, the surgical area should be treated with an antiseptic solution in the sampling field, for instance, in anterior abdominal wall. By means of scalpel the skin incision is performed and from its sides the subcutaneous fat was cut, for instance, in volume of 1 $cm^3$ to 100 $cm^3$.
5. The wounds are closed in accordance with generally accepted surgery procedures.
6. In the puncture/cuts area the singular node sutures are imposed.
7. Any remnants of the antiseptic and biological fluids are washed away from the skin surface by physiological solution with further antiseptic solution treatment for local administration.
8. In the puncture/cuts are sterile drapes and patch are imposed.
9. By means of syringe or blood collection system containing anticoagulant solution, from 1 ml to 400 ml of patient venous peripheral blood were taken.
10. Transportation of anatomical material from surgery room/manipulation room into the biotechnology lab is performed at cool (+4+6° C.) in special thermoboxes for 1-24 hours from the moment of sample collection.
11. Syringes with lipoaspirate, syringes with bone marrow aspiration, syringes/systems with peripheral blood and container with bone fragment were transferred at cool (+4+6° C.) in biotechnology lab for further processing.
12. All consumables that had contact with donor tissues, and biowastes are disinfected by soaking in container with disinfectant solution for 1 hour, and then disposed properly.

STAGE 2 should be performed as follows:
II. Cell isolation, culturing and expansion in the biotechnology lab: bone marrow-derived multipotent mesenchymal stromal/stem cells (MSCs), adipose-derived MSCs, or adipose-derived stem cells, ADSCs, periosteum cells, and endothelial progenitor cells. Manufacturing of the 3D osteoprogenitor prevascularized graft (3D-OPG) at the biotechnology lab.
1. 3D osteoprogenitor prevascularized graft (3D-OPG) consists of cultured autologous or allogeneic: bone marrow-derived or adipose-derived MSCs, or MSCs isolated from other tissues of adult body, cultured periosteum cells (PCs), cultured endothelial precursor cells (EPCs) from peripheral blood or other sources, fibrin or collagen hydrogels and carrier for cells (scaffold).

Figure 2:
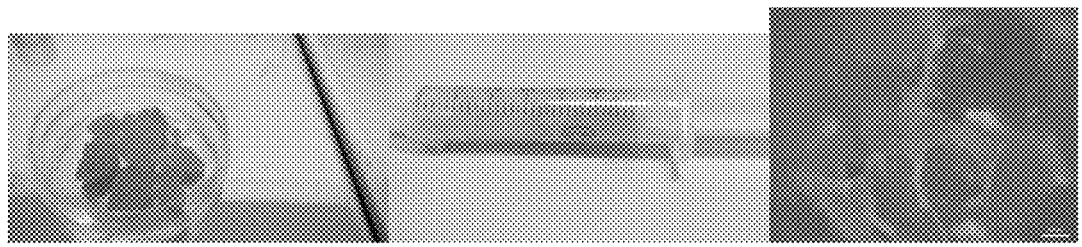
FIG. 2: shows 3D-OPG component view—bone chips (on the left); 3D-OPG based on bone chips (center) and microphotograph of spongy bone chips seeded with cultured cells (on the right); FDA/PI combined stain (quality control on cell seeding efficiency and cell viability).
Figure 3:
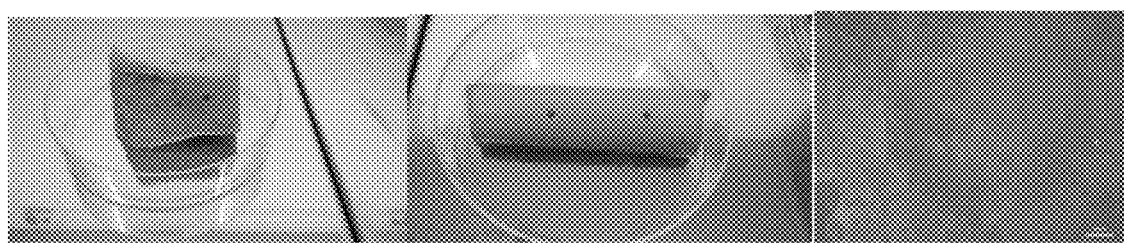
FIG. 3: shows 3D-OPG view based on bone blocks (on the left, center) and microphotograph of compact part of bone block seeded with cultured cells (on the right); FDA/PI combined stain (quality control on cell seeding efficiency and cell viability).
Figure 4:
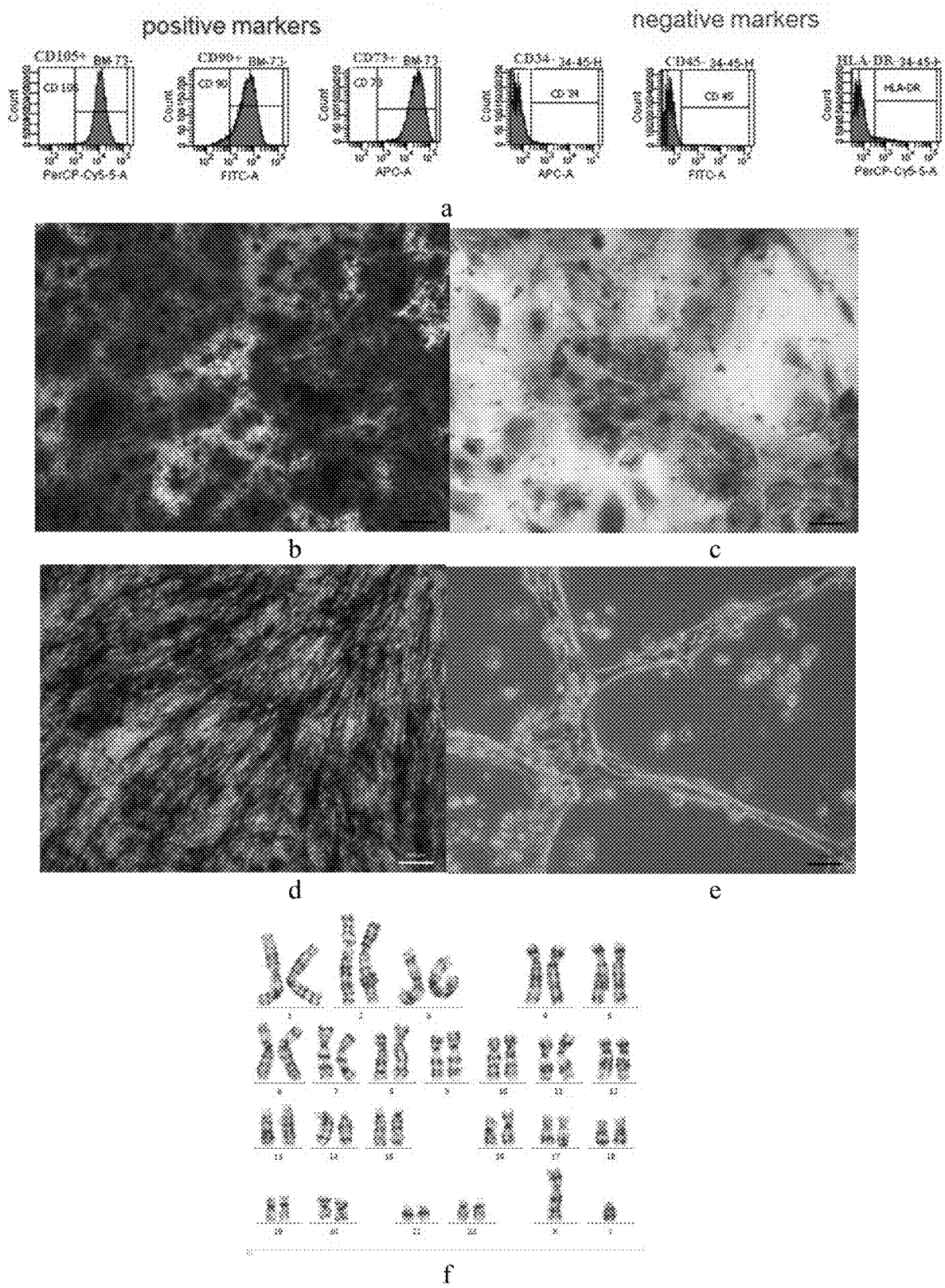
FIG. 4: Functional quality criteria of cell components used for 3D-OPG manufacturing:
a—phenotype of bone marrow-derived MSCs, flow cytometry, cells are positive for CD105+ CD90+ CD73+, negative for CD34− CD45− HLA-DR− (cell type identification);
b—osteogenic differentiation of bone marrow-derived MSCs, Alizarin Red S stain (multipotency);
c—adipogenic differentiation of bone marrow-derived MSCs, Oil Red 0 stain, Romanowsky-Giemsa counter-stain (multipotency);
d—production of acid phosphatase by osteogenic cells of periosteum, BCIP/NBT (cell type identification);
e—capillary-like structures forming by peripheral blood endothelial precursor cells in 3D matrix (cell type identification);
f—cultured peripheral blood endothelial precursor cells karyotype, GTG-banding: normal male karyotype, 46XY.

2. For obtaining of MSCs culture patient red bone marrow aspirate was collected with adding of anticoagulant solution, in amount of 0.01 ml to 100 ml contained in cell culture flasks of 25 cm² to 175 cm² determined as $10^4$-$10^6$ nucleated cells per 1 cm² of a flask and were cultured in growth medium containing: culture medium DMEM:F12, or alpha MEM, or other culture media supplemented with 5-20% fetal calf serum, or 5-20% pooled human thrombocyte lysate, or 5-20% pooled human serum, or 5-20% human autologous thrombocyte lysate, or 5-20% human autologous serum, 0.1-100 ng/ml of bFGF, 100-1000 mM L-glutamine solution, 0.1-100 IU anticoagulant solution and 1-1000 IU/ml antibiotic/antimycotic solution.
3. Cells were cultured in the multi-gas incubator at 24-41° C. and saturated humidity of 60-99% in atmosphere of 1-20% $CO_2$ (carbon dioxide) and 0.1-21% $O_2$ (oxygen) for 3-60 days.
4. Primary culture cells were seeded for expansion into culture flasks for necessary therapeutic dosage obtaining, for instance, 2×10⁸ cells. Cell passaging, or subculturing, into culture flasks is performed by using of admixture of protease solutions or non-enzymatic disaggregation solutions, conventional or commercial.
5. Counting of viable cells in suspension is performed in cell counters, conventional or automatic, with use of 3% acetic acid (counting of all nucleated cells) and 0.4% trypan blue solution (counting of stained dead cells). Cell viability counting is performed as number of viable cells divided by total cell number. Trypan blue stained cells are considered to be non-viable.
6. Then cells are transferred to cryomedium and kept at temperature of −18° C. to −196° C. for a long time period.
7. For obtaining of periosteum cells the bone fragment of any bone of a patient was digested with 0.01%-1% solution of proteolytic enzyme admixture at temperature of 24-41° C. and 5-1000 rpm for 5-1440 minutes.
8. For obtaining ADSCs or MSCs from other tissues, lipoaspirate or patient tissue fragment was treated with 0.01%-1% solution of proteolytic enzyme admixture at 24-41° C. and 5-1000 rpm for 5-1440 minutes.
9. For obtaining EPCs culture 0.1 ml to 400 ml of human blood taken with adding of anticoagulant solution was administered into culture flasks 25 cm² to 1720 cm² at the rate of $10^4$-$10^6$ nucleated cells per 1 cm² of a flask and cultured in growth medium containing: culture medium EBM, EBM-2, EGM, EGM-2, MCDB, DMEM:F12, alpha MEM, or other culture media supplemented with 5-20% fetal calf serum, or 5-20% pooled human thrombocyte lysate, or 5-20% pooled human serum, or 5-20% human autologous thrombocyte lysate, or 5-20% of human autologous serum, cocktail containing 0.1-1000 ng/ml admixture of different growth factors (e.g. VEGF, EGF, bFGF, IGF and others), 100-1000 mM of L-glutamine solution, 0.1-100 MO anticoagulant solution and 1-1000 IU/ml antibiotic/antimycotic solution.
10. Obtained EPCs suspension was administered into culture flasks and cultured in growth medium of following composition: culture medium EBM, EBM-2, EGM, EGM-2, MCDB, DMEM:F12, alpha MEM, or other culture media supplemented with 5-20% fetal calf serum, or 5-20% pooled human thrombocyte lysate, or 5-20% pooled human serum, or 5-20% human autologous thrombocyte lysate, or 5-20% of human autologous serum, cocktail containing 0.1-1000 ng/ml admixture of different growth factors (e.g. VEGF, EGF, bFGF, IGF and others), 100-1000 mM of L-glutamine solution, 0.1-100 MO anticoagulant solution and 1-1000 IU/ml antibiotic/antimycotic solution.
11. Cells were cultured in the multi-gas incubator at 24-41° C. and saturated humidity of 60-99% in atmosphere 1-20% $CO_2$ (carbon dioxide) and 0.1-21% $O_2$ (oxygen) for 3-60 days.
12. Expended cells were transferred to cryomedium and kept at temperature of −18 to −196° C. for a long time period.
13. For manufacturing of cell suspension OPG variant cultured cell types individually (MSCs, periosteum cells and EPCs) or in an admixture of cultured MSCs, periosteum cells and EPCs at ratio 0.5-10:0.1-10:0.1-5, respectively, are resuspended in physiological solution, or in platelet-rich plasma, or in thrombocyte lysate, or in blood serum, or in the other isotonic solution or medium.
14. For manufacturing of hydrogel 3D-OPG variant cultured cell types individually (MSCs, periosteum cells and EPCs) or in an admixture of cultured MSCs, periosteum cells and EPCs at ratio 0.5-10:0.1-10:0.1-5, respectively, are resuspended in fibrin/collagen hydrogel or in a hydrogel of other chemical composition.
15. For manufacturing of entire 3D-OPG variant cultured cell types individually (MSCs, periosteum cells and EPCs) or in an admixture of cultured MSCs, periosteum cells and EPCs at ratio 0.5-10:0.1-10:0.1-5, respectively, are seeded in suspension or in fibrin/collagen hydrogel or in a hydrogel of other chemical composition (FIG. 1), in appropriately treated and sterilized by any method of acellular, hipoimmunogenic, allogeneic/xenogeneic and partially demineralized/non-demineralized: bone blocks of required size and form (FIG. 2), or in bone chips (FIG. 3), or in bone crumbs.
16. Cell-seeded 3D-OPG is incubated into multi-gas incubator at 24-41° C. and saturated humidity of 60-99% in atmosphere of 1-20% $CO_2$ (carbon dioxide) and 0.1-21% $O_2$ (oxygen) for 1-90 days in growth medium of following composition: culture medium DMEM:F12, alpha MEM, or other culture media supplemented with 5-20% fetal calf serum, or 5-20% pooled human thrombocyte lysate, or 5-20% pooled human serum, or 5-20% human autologous thrombocyte lysate, or 5-20% human autologous serum, 0.1-1000 ng/ml bFGF and/or growth factors admixture, cytokines, hormones, small molecules, etc. (e.g. TGFβ superfamily of proteins, BMP, PDGF, VEGF, EGF family, FGF family, Wnt, IGF family and the others), 100-1000 mM L-glutamine solution, 0.1-100 IU anticoagulant solution and 1-1000 IU/ml antibiotic/antimycotic solution.
17. 3D-OPG is transported under cool conditions in the container in transport medium containing DMEM:F12, alpha MEM or the other culture medium, and 1-1000 IU/ml antibiotic/antimycotic solution for 1 or 24 hours.
18. At all stages of 3D-OPG manufacturing and its final release the quality control procedure is applied both for cultured cells and graft seeding for infection agents' absence, cell type identity, normal karyotype, viability, multipotency, activity, seeding efficiency, etc. (FIG. 4).

STAGE 3 should be performed as follows:

I. Storage of the cultured cells under ultra-low temperatures
1. Cryopreserved solution for long term storage of cultured cells contains culture medium DMEM, DMEM: F12, alpha MEM or other culture media supplemented with 5-50% fetal calf serum, or 5-50% pooled human thrombocyte lysate, or 5-50% pooled human serum, or 5-50% human autologous thrombocyte lysate, or 5-50% human autologous serum, or fetal calf serum with adding of 5-50% of cryoprotector, for instance, DMSO, or any other conventional or synthetic cryomedia used with or without xenogeneic substances.
2. Obtained after removal from the culture flask surface and carefully washed with isotonic solution cell suspension designed for low temperature preservation, after nucleated cell counting, mixed with cryopreserved and equilibrate solution for 3-40 min. at +2° C. to +25° C.
3. The cells are preserved in cryovials with capacity of 2.0-5.0 ml at a concentration of $10^3$-$10^8$ cell s/ml.
4. Cryovials with cell suspension are stored for a long time, for instance, 1-10 years, in cryo-depositories, for instance, in Dewar vessels, under liquid nitrogen atmosphere at temperature of −196° C.

STAGE 4 should be performed as follows:

I. Transplantation of the 3D-OPG at the surgery room in case of fracture non-unions (false joints), bone defects and femoral head avascular osteonecrosis 1. Cell transplantation as a suspension or self-polymerizing hydrogel for non-unions or false joints treatment via injection method This transplantation method is used for non-unions and/or false joints, when between bone fragments there is diastasis no more than 1 cm and absence of bone fragments sclerosis. In the case of osteoreparative processes restoration due to non-union and/or false joints is performed in two stages. During the first stage, anatomical material collection is performed for further cell isolation. If necessary the preparative procedures are held, extra-focal transosseous osteosynthesis of bone fragments with external fixation of spoke or spoke-rod or rod type device and removal of present angle deformations. Second stage, particularly cell transplantation as cell suspension or self-polymerizing hydrogel, is performed after obtaining of therapeutic cell number. Cell transplantation is performed in interfragmental region so that transplanted cells infiltrate the entire region. The administration of cells in suspension or self-polymerizing hydrogel is performed in aseptic conditions after antiseptic solution treatment of transplantation site. At first, interfragmental scar attached closely to bone fragments is infiltrated. The injection needle enters until it presses against the bone fragment, then cell suspension or self-polymerizing hydrogel is administered along the bone fragment. After tissue infiltration attaching to bone fragments, cell suspension or self-polymerizing hydrogel is administrated in the interfragmental scar rest until all scar is infiltrated with cells.

2. 3D osteoprogenitorprevascularized graft (3D-OPG) transplantation via surgery method for non-unions and/or false joints with bone fragment sclerosis within and in bone tissue defects In the case of the osteoreparative processes launch for non-union and/or false joints and bone defects restoration the transplantation is performed in two stages. During the first stage anatomical material collection is performed for further cell isolation. If necessary the preparative procedures are held, such as extra-focal transosseous osteosynthesis of bone fragments with external fixation of spoke or spoke-rod or rod type device and removal of present angle deformations. If there are cicatrical and/or scar-ulcer skin defects over non-union or bone defect sites, plastic surgery of skin defects is performed.

3D-OPG volume and shape are determined individually in every case. Transplantation is performed after expansion of therapeutic cell number and the manufacturing of 3D-OPG of required size.

Figure 5:
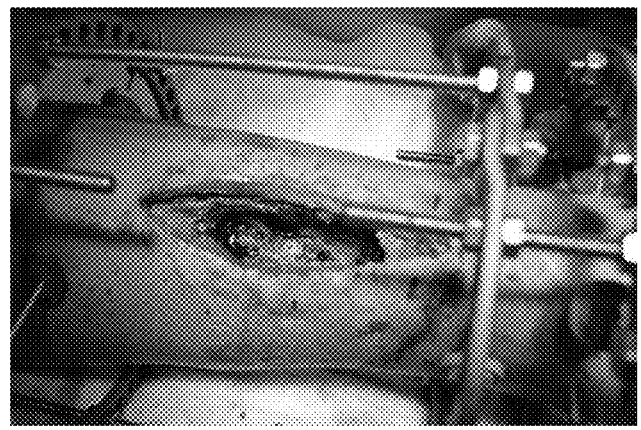
FIG. 5: shows the stages of 3D-OPG transplantation: recipient bed preparation.

Second stage, particularly transplantation of 3D-OPG is performed under surgery room conditions with appropriate anesthetic management. Transplantation starts with recipient wound bed preparation. Longitudinal and/or convex incision were performed to make a free access to non-union or bone defect area. Bone fragments are separated from the surrounding soft tissues, for instance, with a xyster, the area of fracture or bone defect is allocated. All scar tissue located between bone fragments, should be excised carefully. All interfaces of bone fragments and medullary canals are cleansed from scars; medullary canals are opened. Immediately prior to transplantation, recipient bed is washed with antiseptic solution, dried and surrounded by sterile drapes (FIG. 5).

Figure 6:
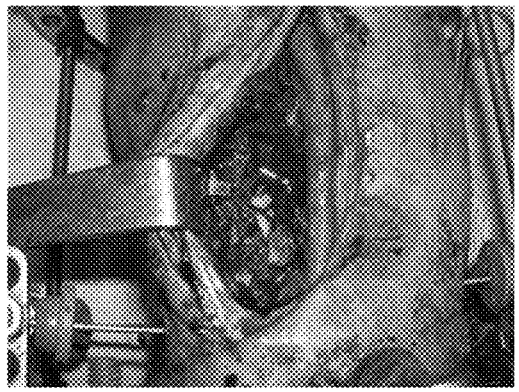
FIG. 6: shows the stages of 3D-OPG transplantation: placement of 3D-OPG based on bone chips in the bone wound.

In long-term non-union and/false joints and tangential (lateral) bone defects used 3D-OPG is based on osteoplastic material, bone chips and/or bone crumbs. Bone chips/crumbs are put closely in recipient bed between bone fragments that they tightly contact the adjacent bone tissue of recipient bed and contact between each other (FIG. 6). Bone fragments fixation is performed with external fixation of spoke or spoke-rod or rod type device, or extramedullary plate. Soft tissues under transplant are sutured layer-by-layer closely. Transplantation area is actively and passively drained for desired time.

Figure 7:
FIG. 7: shows the stages of 3D-OPG transplantation: placement of 3D-OPG based on bone block in the bone wound and its fixation with a plate.

Generally, in complete (circular) bone defects 3D-OPG in form of bone block is used. The ends of proximal and distal bone fragments are polished by means of sawblade so that ends of bone fragments are perpendicular to bone axis. Bone block is placed into defect and attached to bone fragments by means of external fixation of spoke or spoke-rod or rod type device, or extramedullary plate, or intramedullary pins (FIG. 7). Between bone fragments and 3D-OPG the compression is created. Soft tissues under transplant are sutured layer-by-layer closely. Transplantation area is actively and passively drained for desired time.

Example

Transplantation of 3D Osteoprogenitorprevascularized Graft (3D-OPG) in Femoral Head Avascular Osteonecrosis (Transcervical Intracapital Transplantation)

Osteoreparative processes restoration in necrotic areas of femoral neck is performed in two stages. Every stage is performed in the surgery room under appropriate anesthetic management with use of X-ray control (electron-optical image intensifier, EOII).

During the first stage, after surgery field treatment, anatomical material collection performed for further cell isolation. In the external femoral skin surface in projection of subtrochanteric region of the femur, the skin is pricked with pin of <3 mm in diameter. After the pin presses against the bone, the pin is directed in accordance with femoral neck direction and with the help of a drill under EOII control, the pin is led through neck into femoral head. The pin should reach femoral head osteonecrosis region. Skin is cut 1 cm longitudinally to the pin. By means of cannulated drills leading along the pin, bone channel of required diameter is performed. It starts in subtrochanteric region of the femur and ends in femoral head osteonecrosis region. The pin is removed and the skin is sutured. After this, the pin pricks the skin in the projection of top of greater trochanter and under EOII control, the pin is led along the femur that it leads through all trochanter and enters the femoral medullar channel. By means of scalpel, skin is cut longitudinally to the pin over 1 cm. By means of cannulated drills, for instance, from 6 to 10 mm in diameter, leading along the spin, bone channel is forming. It starts on the top of the greater trochanter and ends in subtrochanteric region of the femur. The pin is removed and the skin is sutured.

Second stage, particularly transplantation, is performed after expansion of required cell number and manufacturing of 3D-OPG based on bone chips and/or bone crumbs. Cell number and 3D-OPG size are determined individually in every case.

In the surgery room after appropriate anesthesia and antiseptic treatment of surgery field, with the scalpel on the external femoral surface in subtrochanteric region, it is performed a longitudinal incision of skin and bone surrounding tissues. In subtrochanteric region there is an external inlet of bone channel. Due to drills, for instance, from 10 to 14 mm in diameter, under EOII control, the extending of bone channel in femoral neck and head is performed, and with the surgical instruments, osteonecrosis zone of femoral head is destroyed. Destroyed necrotic bone tissue is extracted. Through the bone channel the head cavity is made and longitudinally to bone channel the 3D-OPG based on hydrogel and/or bone chips/crumbs is administrated. Hydrogel and/or bone chips/crumbs are put closely in such a way that they fully fill the cavity created in the head after the necrotic bone tissue extraction, and the bone channel in femoral neck. In 3D-OPG based on hydrogel and/or bone chips/crumbs and longitudinal to femoral neck axis, channel forms for the entire femoral neck for osteoreparative processes run. The wound is sutured layer-by-layer and actively and/or passively drained for appropriate time.

The disclosure herein include(s) at least the following aspects:

Aspect 1: Medical product and/or preparation based on human cells (cell and/or tissue transplant) as cell compound for osteoreparative processes alteration correction and/or bone defects restoration, wherein the active component comprising viable cultured, autologous, allogenic cells individually and/or in compound as follows: multipotent mesenchymal stem and/or stromal cells isolated from bone marrow, and/or fat tissue, and/or other tissues and/or human organs (including but not limited to fetal tissue and/or fetoplacental complex tissues), osteoprogenitor periosteum, endosteum and/or bone cells, and/or endothelial precursor cells, endothelial cells.

Aspect 2: Medical product and/or preparation based on human cells (cell and/or tissue transplant) as self-polymerizing fibrin, collagen, other hydrogel with cells for correction of osteoreparative processes alteration and/or bone defect restoration, wherein the active component comprises viable cultured, autologous, allogenic cells individually and/or in compound as follows: multipotent mesenchymal stem and/or stromal cells isolated from bone marrow, and/or fat tissue, and/or other tissues and/or human organs (including but not limited to fetal tissue and/or fetoplacental complex tissues); osteoprogenitor periosteum, endosteum and/or bone cells; and/or endothelial precursor cells, endothelial cells.

Aspect 3: Medical product and/or preparation based on human cells (cell and/or tissue transplant) as 3D prevascularized osteoprogenitor graft (hereinafter referred to as "3D-OPG") for correction of osteoreparative processes alteration and/or bone defect restoration, comprising cell carrier, such as e.g. scaffold and/or matrix, appropriately treated, sterile, acellular, apyrogenic, autologous, allogeneic, xenogeneic, synthetic, partly demineralized, non-demineralized, wherein bone-block-based of required size and/or form, bone chips, bone crumbs; self-polymerizing fibrin, collagen, other hydrogel; as an active component; 3D-OPG comprises viable cultured, autologous, allogenic cells individually and/or in compound as follows: multipotent mesenchymal stem and/or stromal cells isolated from bone marrow, and/or fat tissue, and/or other tissues and/or human organs (including but not limited to fetal tissue and/or fetoplacental complex tissues); osteoprogenitor periosteum, endosteum and/or bone cells; and/or endothelial precursor cells, endothelial cells.

Aspect 4: Medical product and/or preparation based on human cells (cell and/or tissue transplant) according to aspect 1, 2 and 3 farther comprising individual cultured cell types and/or compound of different cell types in certain ratio.

Aspect 5: Medical product and/or preparation based on human cells (cell and/or tissue transplant) according to aspect 3 wherein cultured cells are seeded directly on/in carrier, such as e.g. scaffold and/or matrix, comprising self-polymerizing fibrin, collagen, other hydrogel.

Aspect 6: Medical product and/or preparation based on human cells (cell and/or tissue transplant) according to aspect 3 wherein 3D-OPG for 1-90 days might be incubated under conditions of multi-gas incubator to the extent of its uniform seeding with cultured cells and/or scaffold-guided osteogenic differentiation in 3D-OPG functional structure.

Aspect 7: Method of the osteoreparative processes' correction and/or bone defect restoration by means of human cell-based products (cell and/or tissue transplants) according to aspects 1, 2 and 3 wherein transplantation comprises two stages: 1) anatomical material collection, its expansion and/or storage, performance of general preparative surgery procedures; further 2) performance of medical product and/or preparation transplantation based on human cells (cell and/or tissue transplants).

Aspect 8: Method of the osteoreparative processes' correction and/or bone defect restoration by means of human cell-based products (cell and/or tissue transplants) according to aspect 7, wherein osteoreparative processes restoration in avascular osteonecrosis of femoral head might be performed in two stages: 1) anatomical material collection, its expansion and/or storage, performing of decompression osteotrepanation of head and/or greater trochanter of femur; 2) performance of medical product and/or preparation transplantation based on human cells (cell and/or tissue transplants) while prior to transplantation the bone necrosis area might be destroyed, as its extraction with surgical instruments by means of forming a channel comprising 3D-OPG based on bone chips and/or crumbs along the femoral neck.

Aspect 9: Medical product and/or preparation based on human cells (cell and/or tissue transplants) according to aspects 7 and 8 wherein the transplantation might be performed by injection and/or surgery methods.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A medicinal product comprising
viable co-cultured human cells comprising:
multipotent mesenchymal stromal cells isolated from bone marrow (BM-MSCs),
osteogenic periosteum cells (PCs), and
endothelial progenitor cells (EPCs),
combined at a BM-MSCs:PCs:EPCs ratio of 1-3:1-3:1 prior to co-cultivation.

2. A hydrogel medicinal product comprising
a hydrogel comprising fibrin, collagen, or a combination thereof; and
viable co-cultured human cells comprising:
multipotent mesenchymal stromal cells isolated from bone marrow (BM-MSCs),
osteogenic periosteum cells (PCs), and
endothelial progenitor cells (EPCs),
the cells resuspended in the hydrogel at a BM-MSCs:PCs:EPCs ratio of 1-3:1-31 prior to co-cultivation.

3. A three dimensional prevascularized osteoprogenitor graft, comprising
a cell carrier, wherein the cell carrier comprises
a hydrogel comprising fibrin, collagen, or a combination thereof;
a bone chip, or a bone crumb; or
a combination thereof;
and viable co-cultured human cells comprising:
multipotent mesenchymal stromal cells isolated from bone marrow (BM-MSCs),
osteogenic periosteum cells (PCs), and
endothelial progenitor cells (EPCs),
the cells seeded in the cell carrier at a BM-MSCs:PCs:EPCs ratio of 1-3:1-3:1 prior to co-cultivation.

4. The graft according to claim 3 wherein after seeding the cell carrier with the cells, the seeded cell carrier is incubated for 1-90 days under conditions in a multi-gas incubator to obtain the graft.

5. The medicinal product of claim 1, wherein the osteogenic periosteum cells are isolated from a fibula bone sample.

6. The medicinal product of claim 1, wherein the EPCs are isolated from peripheral blood.

7. The graft of claim 3, wherein the bone block, bone chip, or bone crumb is allogeneic or xenogeneic to the patient.

8. A method of treating a human patient in need of osteoreparative correction of avascular osteonecrosis, a fracture non-union, a false joint, a bone defect, or a combination thereof, comprising
administering the medicinal product of claim 1 through an injection needle to a transplantation site in a human patient such that the cells infiltrate the transplantation site, wherein the transplantation site comprises a site of avascular osteonecrosis, a fracture non-union, a false joint, a bone defect site, or a combination thereof.

9. The method of claim 8, wherein the medicinal product further comprises a hydrogel comprising fibrin, collagen, or a combination thereof.

10. The method of claim 8, further comprising
collecting an anatomical material from the human patient or an allogeneic donor,
isolating the cells from the anatomical material; and
expanding the cells by cell culture to a number required by the human patient.

11. A method of treating a human patient in need of osteoreparative process correction of avascular osteonecrosis, a fracture non-union, a false joint, a bone defect, or a combination thereof, comprising
surgically transplanting the graft of claim 3 into a site of avascular osteonecrosis, a fracture non-union, a false joint, or a hone defect site in a human patient.

12. The method of claim 11, wherein the cell carrier comprises a hydrogel comprising fibrin, collagen, or a combination thereof.

13. The method of claim 11, wherein the cell carrier comprises a bone block of a size and form required by the patient, a bone chip, or a bone crumb.

14. The method of claim 11, further comprising
collecting an anatomical material from the human patient or an allogeneic donor,
isolating the cells from the anatomical material;
expanding the cells by cell culture to a number required by the human patient; and
seeding the cell carrier with the cells.

15. A method of making the medicinal product of claim 1, comprising
collecting an anatomical material from a human patient or an allogeneic donor,
isolating from the anatomical material multipotent mesenchymal stromal cells from bone marrow (BM-MSCs), osteogenic periosteum cells (PCs), and endothelial progenitor cells (EPCs);
expanding the cells by cell culture to a number required by the human patient; and
resuspending the cells in a medium in a BM-MSCs:PCs:EPCs ratio of 1-3:1-3:1; and
co-cultivating the resuspended cells to obtain the medicinal product of claim 1.

16. The method of claim 15, further comprising
seeding a cell carrier with the BM-MSCs, PCs, and EPCs in a BM-MSCs:PCs:EPCs ratio of 1-3:1-3:1.

17. The method of claim 16, wherein the cell carrier comprises
a hydrogel comprising fibrin, collagen, or a combination thereof;
a bone chip, or a bone crumb; or
a combination thereof.

* * * * *